(12) United States Patent
Talish et al.

(10) Patent No.: US 6,432,070 B1
(45) Date of Patent: Aug. 13, 2002

(54) METHOD AND APPARATUS FOR ULTRASONIC TREATMENT OF REFLEX SYMPATHETIC DYSTROPHY

(75) Inventors: Roger J. Talish, Hillsborough, NJ (US); Alan A. Winder, Westport, CT (US)

(73) Assignee: Exogen, Inc., Piscataway, NJ (US)

( * ) Notice: Subject to any disclaimer, the term of this patent is extended or adjusted under 35 U.S.C. 154(b) by 0 days.

(21) Appl. No.: 09/568,481

(22) Filed: May 9, 2000

Related U.S. Application Data

(60) Provisional application No. 60/133,442, filed on May 11, 1999.

(51) Int. Cl.[7] .................................................. A61H 1/00
(52) U.S. Cl. ........................... 601/2; 600/437; 600/439; 601/3
(58) Field of Search ...................... 601/2, 1, 3; 600/437, 600/439

(56) References Cited

U.S. PATENT DOCUMENTS

| | | | | |
|---|---|---|---|---|
| 3,828,769 A | * | 8/1974 | Mettler | |
| 4,570,640 A | * | 2/1986 | Barsa | |
| 5,413,550 A | * | 5/1995 | Castel | |
| 5,460,595 A | * | 10/1995 | Hall et al. | |
| 5,556,372 A | * | 9/1996 | Talish et al. | |
| 5,762,616 A | * | 6/1998 | Tlish | |
| 6,206,843 B1 | * | 3/2001 | Iger et al. | |

* cited by examiner

Primary Examiner—Marvin M. Lateef
Assistant Examiner—Jeoyuh Lin
(74) Attorney, Agent, or Firm—Bruce D. Gray; Kilpatrick Stockton LLP

(57) ABSTRACT

The invention relates to apparatus and method for therapeutically treating reflex sympathetic dystrophy using ultra sound. The apparatus includes at least one ergonomically constructed ultrasonic transducer configured to cooperate with a placement module or strip for placement in proximity to pain receptors of the sympathetic nervous system. The apparatus also utilizes a portable, ergonomically constructed main operating unit constructed to fit within a pouch worn by the patient. In operation, at least one ultrasonic transducer positioned in proximity to the pain receptors of the sympathetic nervous system is excited for a predetermined period of time. To ensure that at least one ultrasonic transducer is properly positioned, and to insure compliance with a treatment protocol, a safety interlock is provided to prevent inadvertent excitation of the at least one ultrasonic transducer. In an alternate embodiment, the apparatus includes a treatment basin having a plurality of ultrasonic transducer assemblies placed on the perimeter thereof. The patient places an injured part of the body therein and the transducer assemblies are excited to impinge ultrasonic waves to the injured part of the body.

17 Claims, 22 Drawing Sheets

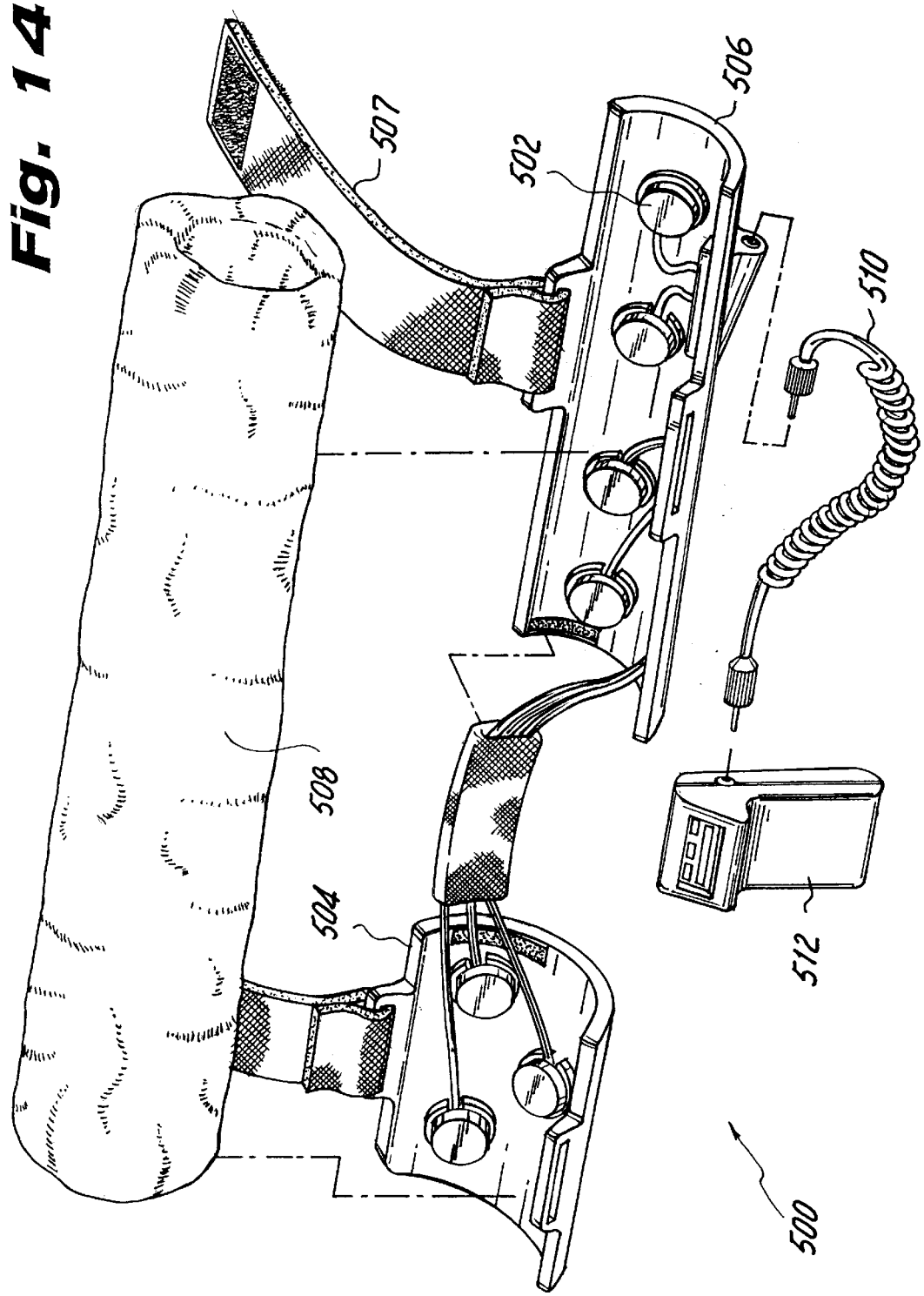

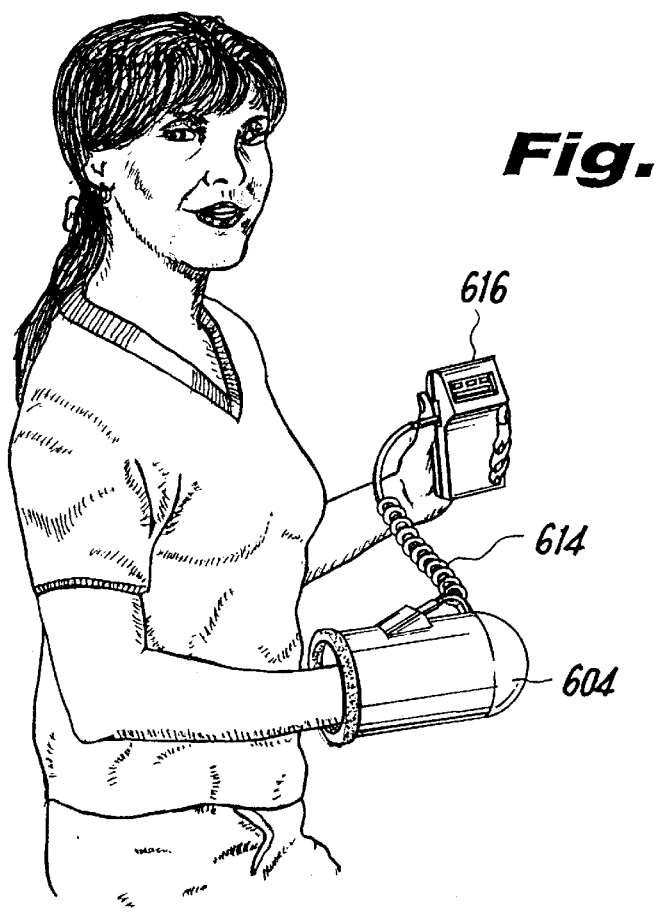
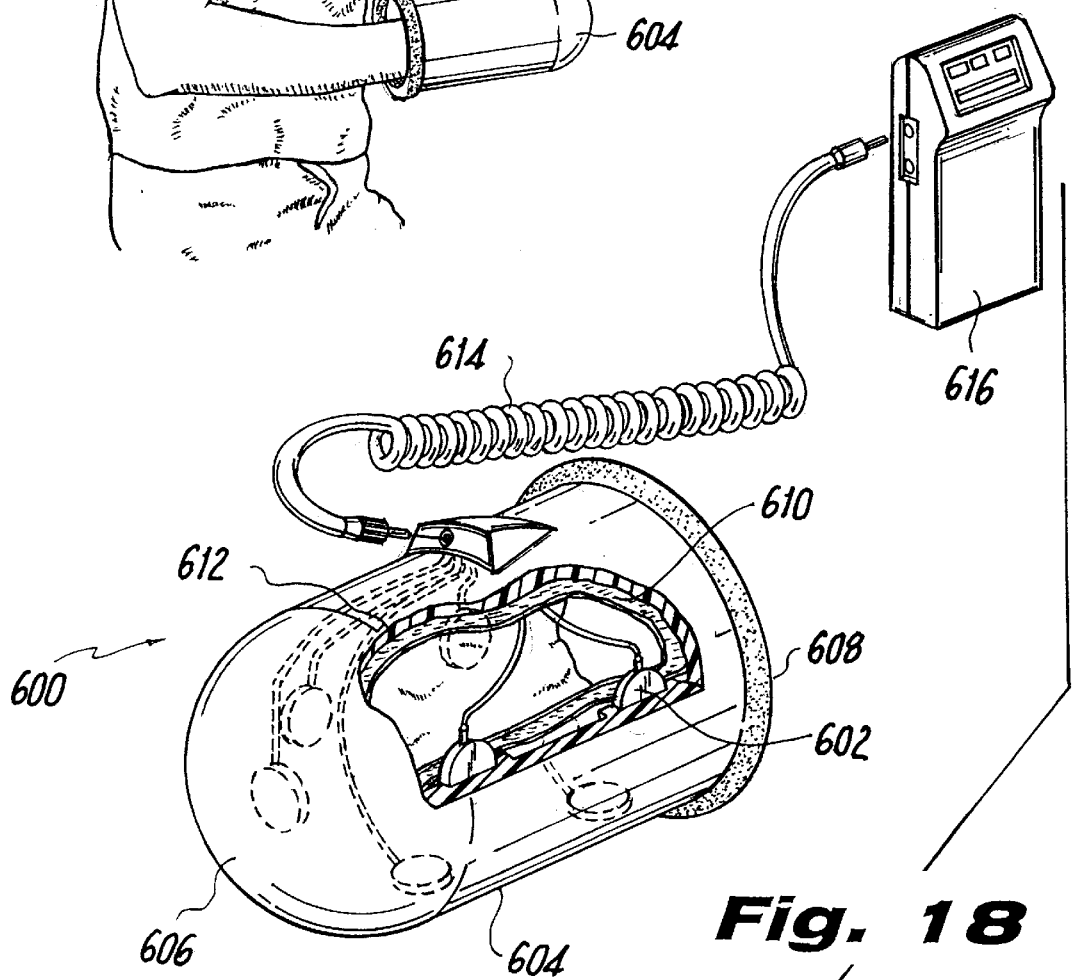

METHOD AND APPARATUS FOR ULTRASONIC TREATMENT OF REFLEX SYMPATHETIC DYSTROPHY

This application claims priority from provisional application No. 60/133,442, filed May 11, 1999.

BACKGROUND OF THE INVENTION

1. Field of the Invention

The present invention relates to a method and apparatus for therapeutically treating injuries using ultrasound. More particularly, the present invention relates to a method and apparatus which utilizes an ergonomically constructed ultrasonic transducer configured to cooperate with a placement module for placement in proximity to any part of the body for therapeutically treating reflex sympathetic dystrophy.

2. Description of the Related Art

The use of ultrasound. to therapeutically treat and evaluate bone injuries is known. Impinging ultrasonic pulses having appropriate parameters; e.g., frequency, pulse repetition, and amplitude, for suitable periods of time and at a proper external location adjacent to a bone injury has been determined to accelerate the natural healing of, for example, bone breaks and fractures.

U.S. Pat. No. 4, 530,360 to Duarte describes a basic non-invasive therapeutic technique and apparatus for applying ultrasonic pulses from an operative surface placed on the skin at a location adjacent a bone injury. The applicator described in the Duarte patent has a plastic tube which serves as a grip for the operator, an RF plug attached to the plastic tube for connection to an RF source, and internal cabling connected to an ultrasonic transducer. To apply the ultrasound pulses during treatment. an operator must manually hold the applicator in place until the treatment is complete. As a result, the patient is, in effect, immobilized during treatment. The longer the treatment period, the more the patient is inconvenienced. The Duarte patents as well as U.S. Pat. No. 5,520,612 to Winder et al. describe ranges of RF signal for creating the ultrasound, ultrasound power density levels, ranges of duration for each ultrasound pulse, and ranges of ultrasonic pulse frequencies.

U.S. Pat. No. 5,003,965 to Talish et al. relates to an ultrasonic body treatment system having a body-applicator unit connected to a remote control unit by sheathed fiber optic lines. The signal controlling the duration of ultrasonic pulses and the pulse repetition frequency are generated apart from the body-applicator unit. Talish et al. also describes a mounting fixture for attaching the body-applicator unit to a patient so that the operative surface is adjacent the skin location.

While the systems described in these patents relate to therapeutic methods and apparatus for ultrasonic treatment there is a need for ergonomically configured signal generators and transducers which permit patient mobility during the treatment of reflex sympathetic dystrophy (RSD). Further, a need exists for an apparatus which optimizes the treatment of RSD while maintaining patient mobility.

RSD is a disease of the sympathetic nervous system, which is one of the components of the central nervous system. The sympathetic nervous system responds to an injury by activating the pain receptors in the injured part of the body. These pain receptors are activated by signals sent by the sympathetic nervous system through neurotransmitters which transmit neural impulses from one neuron to another. This pain acts as a warning to the injured person that they have been hurt, and that they need to stop whatever they are doing in order to prevent further injury. RSD prolongs this normal sympathetic response to an injury by causing the sympathetic nervous system to continue to stimulate the pain receptors long after the injury has healed. Unless the RSD patient is successfully treated, the pain continues unabated for the rest of his/her life.

Several treatments for RSD include drug therapy; spinal blocks which are administered to the patient by injection into the spine; physical therapy; a transcutaneous electrical nerve stimulator (TENS) that connects to the affected area via electrodes and creates electrical pulses that are supposed to interrupt the pain generation and create serotonin and stimulate the release of endorphins; sympathectomy; and implantable devices, such as a peripheral nerve stimulator.

SUMMARY OF THE INVENTION

The ultrasonic treatment apparatus of the present invention may be used for therapeutically treating reflex sympathetic dystrophy (RSD) using ultrasound. The apparatus may include an ergonomically constructed placement module configured for mounting at least one ultrasonic transducer assembly with an integral signal generator which provides excitation signals to ultrasonic transducers within the transducer assembly. Timing control circuitry as well as monitoring circuitry for the proper attachment and operation of the transducer assembly are housed within a portable main operating unit constructed to fit within a pouch worn by the patient. In operation, the placement module is positioned against a part of the patient's body such that at least one transducer is positioned over pain receptors of the sympathetic nervous system. The placement module is preferably placed against the part of the patient's body where it has been medically determined includes pain receptors which are continuously being stimulated by the sympathetic nervous system long after the injury has healed. At least one transducer is then excited for a predetermined period of time to impinge ultrasonic waves against the pain receptors. A sensor may also be used for sensing stimulation of the pain receptors before the at least one transducer is excited.

Accordingly, there is provided a kit suitable for ultrasonically treating reflex sympathetic dystrophy while maintaining patient mobility, which comprises:

an ultrasonic transducer assembly having at least one ultrasonic transducer;

a placement module configured to be worn by a patient, said placement module being configured to receive said transducer assembly such that when said placement module is worn, said at least one ultrasonic transducer is positioned in proximity to pain receptors of the sympathetic nervous system;

an ultrasonic signal generator positioned in said ultrasonic transducer assembly;

a main operating unit; and a sensor coupled to said main operating unit for sensing stimulation of said pain receptors.

Preferably, the main operating unit has an internal power source for powering the signal generator circuitry, a display coupled to the signal generator circuitry to display treatment sequence data, a keypad coupled to the signal generator circuitry to permit user operation and/or entry of data. The signal generator circuitry includes a processor, means for generating a pulsed control signal, and a switch coupled to the processor for regulating the pulsed control signal. A communication interface may be connected between a communication port and the processor to provide a communication link between the ultrasonic signal generator and an external computer or modem. Preferably, the communication interface is a serial communication interface, however, a parallel interface is also contemplated. An alarm is provided to indicate to the user that the treatment time has expired. The alarm is coupled to the processor such that when ultrasonic treatment is completed the processor activates the alarm and terminates ultrasound generation.

The present invention also provides a kit for ultrasonically treating RSD while maintaining patient mobility. The kit includes an ultrasonic transducer assembly, a sensor for sensing the stimulation of the pain receptors, a placement module configured to be worn by a patient and to receive the ultrasonic transducer assembly, an integrated ultrasonic signal generator located in the ultrasonic transducer assembly, a main operating unit (MOU) or controller and a pouch constructed to receive the MOU. Preferably, the MOU has an internal power source and is fitted within a pouch which is releasably secured to a patient during treatment thereby providing patient mobility. A MOU envisioned for use with the present invention is described in U.S. Pat. No. 5,556,372 to Talish et al. which is hereby incorporated by reference.

The MOU is electrically coupled to at least one transducer secured to the placement module and at least one sensor. The signal generator corresponding to each transducer is activated when one or more of the sensors sense the pain receptors being stimulated by the sympathetic nervous system. The activation of a signal generator excites at least one ultrasonic transducer for impinging ultrasonic waves to the pain receptors in the injured part of the body.

A method for ultrasonically treating RSD while maintaining patient mobility is also provided. Once the location of the pain receptors in the injured part of the body is ascertained, for example, by one or more of the sensors, a placement module containing an ultrasonic transducer assembly having at least one transducer and one signal generator is affixed to the injured part of the body such that at least one transducer is in proximity to the pain receptors for the treatment of RSD.

In an alternative embodiment, a series of transducers are attached to a placement module and are controlled by a MOU. In another embodiment, a placement module is provided for securing a plurality of transducers thereto in a plurality of configurations.

Further, the present invention also provides a strip having at least one ultrasonic transducer secured thereto for placement on the patient's body directly above the pain receptors for the treatment of RSD.

BRIEF DESCRIPTION OF THE DRAWINGS

Preferred embodiments of the invention are described below with reference to the drawings, which are described as follows:

FIG. 14 is a perspective view of a portable treatment apparatus of a fifth embodiment configured for treating RSD;

FIG. 15 is a perspective view of a patient wearing. the portable treatment apparatus of FIG. 14;

FIG. 18 is a perspective view of a treatment apparatus of a seventh embodiment configured for treating RSD;

FIG. 19 is a perspective view of a patient using the treatment apparatus of FIG. 18;

DETAILED DESCRIPTION OF THE PREFERRED EMBODIMENTS

The ultrasonic treatment apparatus of the present invention is used for the surgically non-invasive utilization of ultra high-frequency acoustic energy in the treatment of reflex sympathetic dystrophy (RSD). Even though this detailed description discusses the treatment of RSD following an injury, the ultrasound treatment apparatus can be used to treat RSD caused by other means, such as surgery, medication, or an infection. The treatment of other musculoskeletal injuries including cranial and venous ulcers are also contemplated with the present invention.

The apparatus includes an ergonomically constructed placement module having a strap or other fastening means for being secured to an injured part of a patient's body. At least one ultrasonic transducer assembly partially fabricated with a conductive plastic material is attached or imbedded within the placement module and properly positioned in proximity to the pain receptors in the injured part of the body. Different types of ultrasonic transducers and signals can be provided, such as those described and schematically depicted in U.S. Pat. No. 5,520,612 to Winder et al. which is hereby incorporated by reference. Particularly, the transducers and arrangements schematically depicted by FIGS. 7–11 of the patent in which at least one transducer is used to provide acoustic energy to the site of the injury. The apparatus also utilizes a portable, ergonomically constructed main operating unit (MOU) which is constructed to fit within a pouch worn by the patient using belt and shoulder strap and provides control signals to the ultrasonic transducers. The MOU which is utilized is preferably the one described in U.S. Pat. No. 5,556,372 to Talish et al. which is hereby incorporated by reference.

Figure 1:
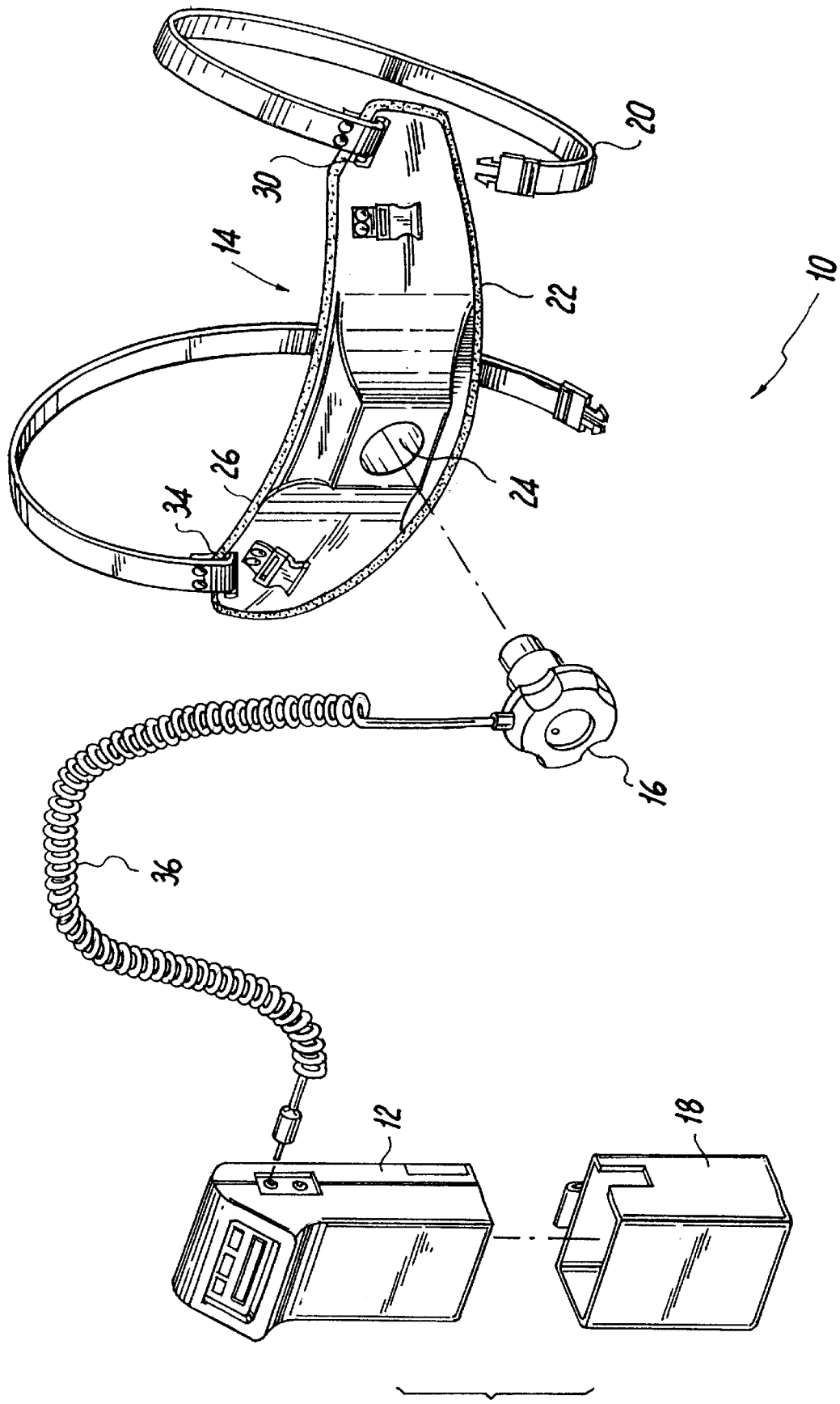
FIG. 1 is a perspective view with parts separated of a first embodiment of a portable ultrasonic treatment apparatus according to the present invention, illustrating a main operating unit or controller and a placement module.

Turning to the figures, in particular FIG. 1, one embodiment of the portable ultrasonic treatment apparatus 10 of the present invention is shown. The ultrasonic treatment apparatus 10 includes a MOU 12, a placement module 14, an ultrasonic transducer assembly 16, and a pouch 18 for releasably securing the MOU 12 to the patient during treatment for providing patient mobility. The placement module 14 is comprised of placement bands 20 and placement support 22. The placement support 22 includes a pocket 24 adapted for placement of the ultrasonic transducer assembly 16 therein. The placement support 22 further includes a body rest 26 having slots 30 for connecting the placement support 22 to the placement bands 20. A sponge-like material 34 lines the inner surface of the placement support 22 for providing comfort to the patient. The placement support 22 may be construed of hard plastics which may be custom molded for a particular patient.

The transducer assembly 16 includes circuitry, schematically illustrated by FIGS. 4 and 4A and described below, for exciting at least one transducer therein and is coupled to the MOU by cable 36. The cable 36 is preferably a multiconductor cable capable of transmitting relatively low frequency RF or optical signals, as well as digital signals. The cable 36 may include coaxial cable or other types of suitable shielded cable. Alternatively, the cable 36 may include fiber optic cable for transmitting optical signals. The signals may be transmitted continuously or as a series of pulses.

Figure 2:
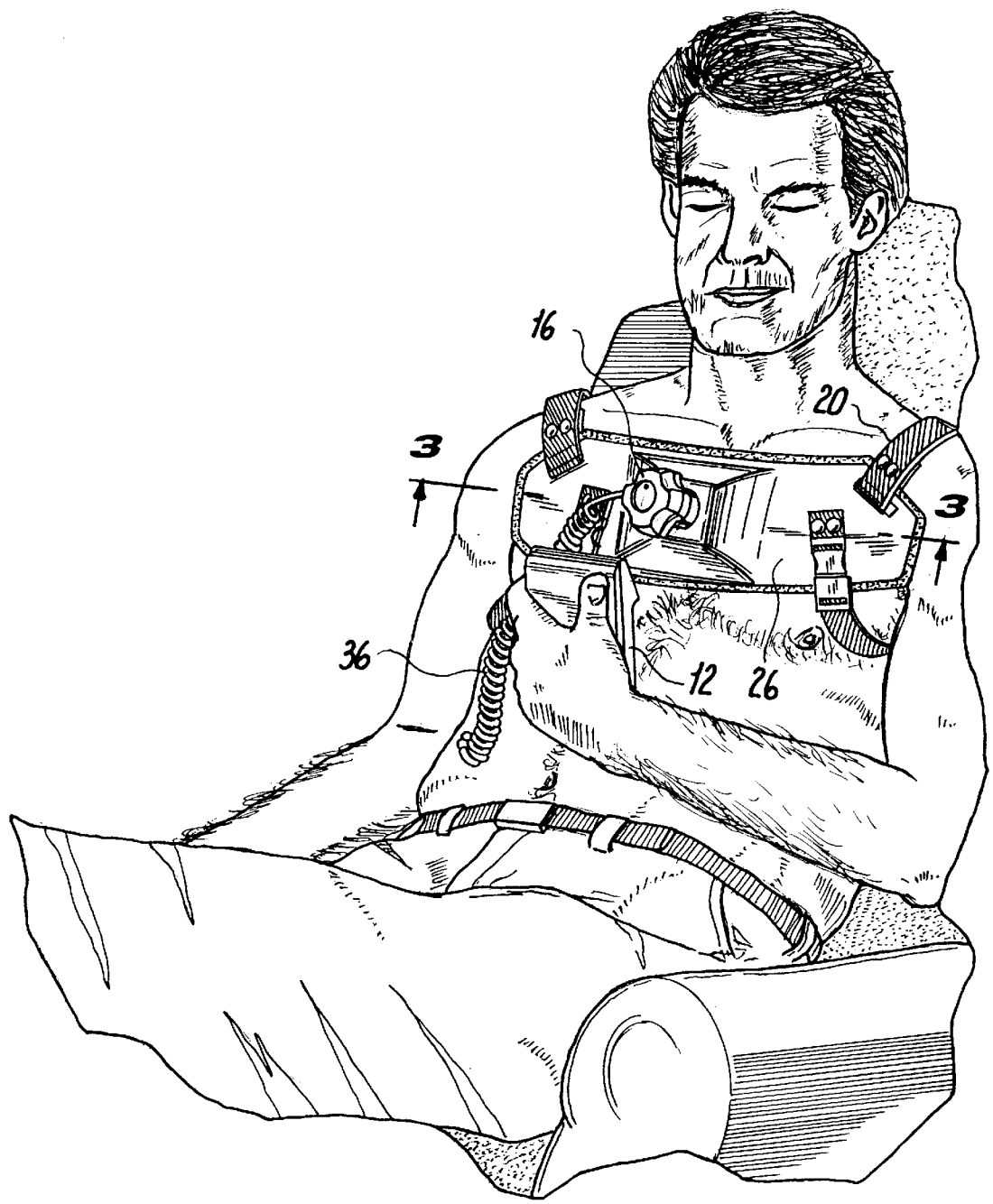
FIG. 2 is a perspective view of a patient wearing the portable treatment apparatus of FIG. 1.
Figure 3:
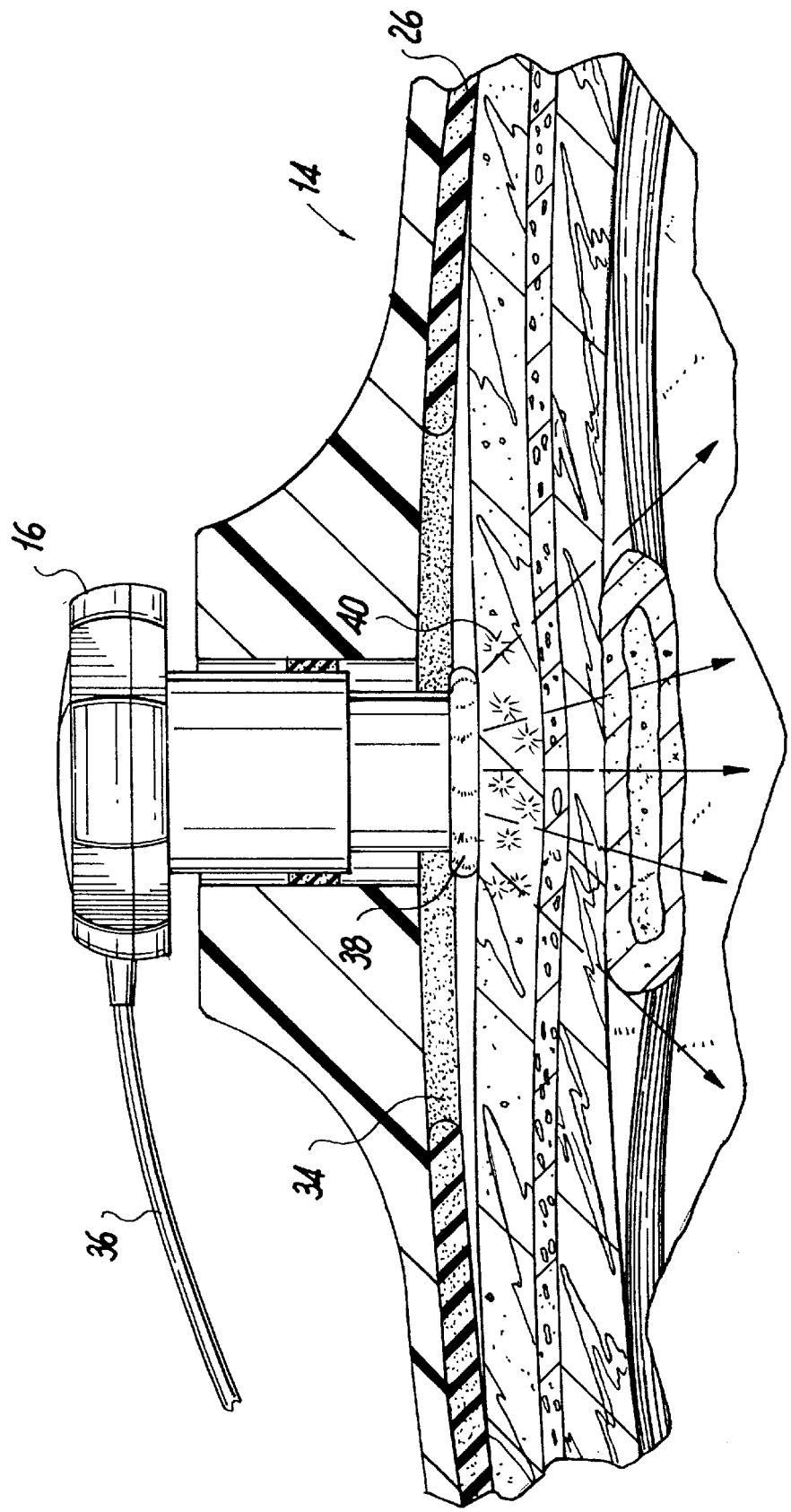
FIG. 3 is a cross-sectional view along line 3—3 in FIG. 2 illustrating the transducer assembly impinging ultrasonic waves to pain receptors where a gel-like substance is positioned between the transducer assembly and the patient's body.

In operation, the placement module 14 is positioned and secured to the patient's body as shown by FIG. 2, such that the transducer assembly 16 lies over the pain receptors of the sympathetic nervous system in the injured part of the body. A locating ring such as the one disclosed in U.S. patent application Ser. No. 08/389,148 may be used for determining the location of injured bone in the case of a bone injury before the placement module 14 is secured to the patient. Once the placement module 14 is properly positioned, the transducer within the transducer assembly 16 is excited for a pre-determined amount of time. A gel-like substance 38 may be positioned between the transducer assembly 16 and the injured part of the patient's body to prevent attenuation of the ultrasonic waves as they travel to the pain receptors 40, as shown by FIG. 3.

Figure 4:
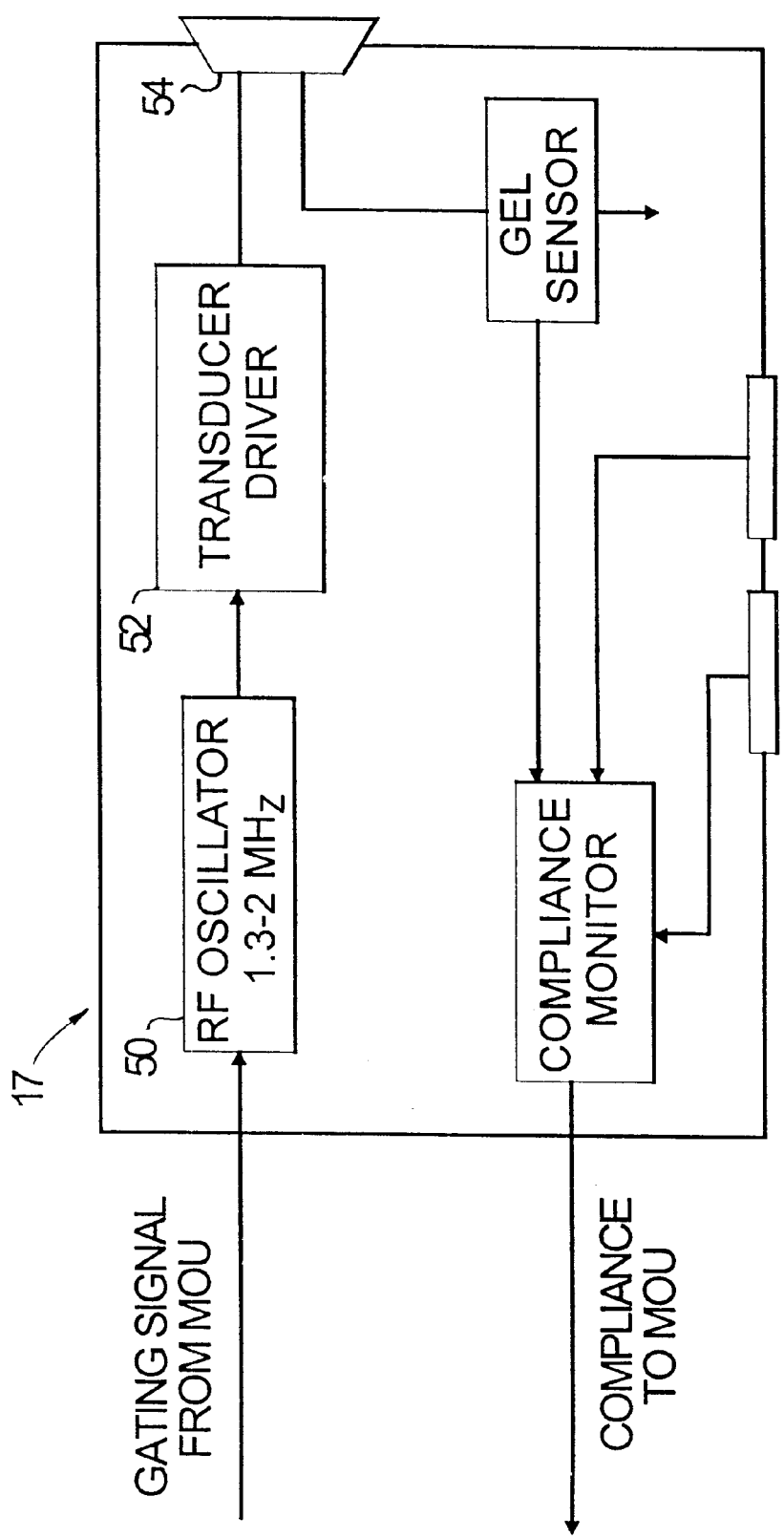
FIG. 4 is a block diagram of one embodiment of the circuitry for the ultrasonic transducer assembly.

With reference to FIG. 4, a block diagram of one embodiment of the ultrasonic transducer assembly circuitry is shown. The transducer assembly circuitry 17 includes a receiver 50 which receives the signals transferred by a signal generator within MOU 12 via cable 36. Receiver 50 is connected to transducer driver 52 which excites transducer 54.

Figure 4A:
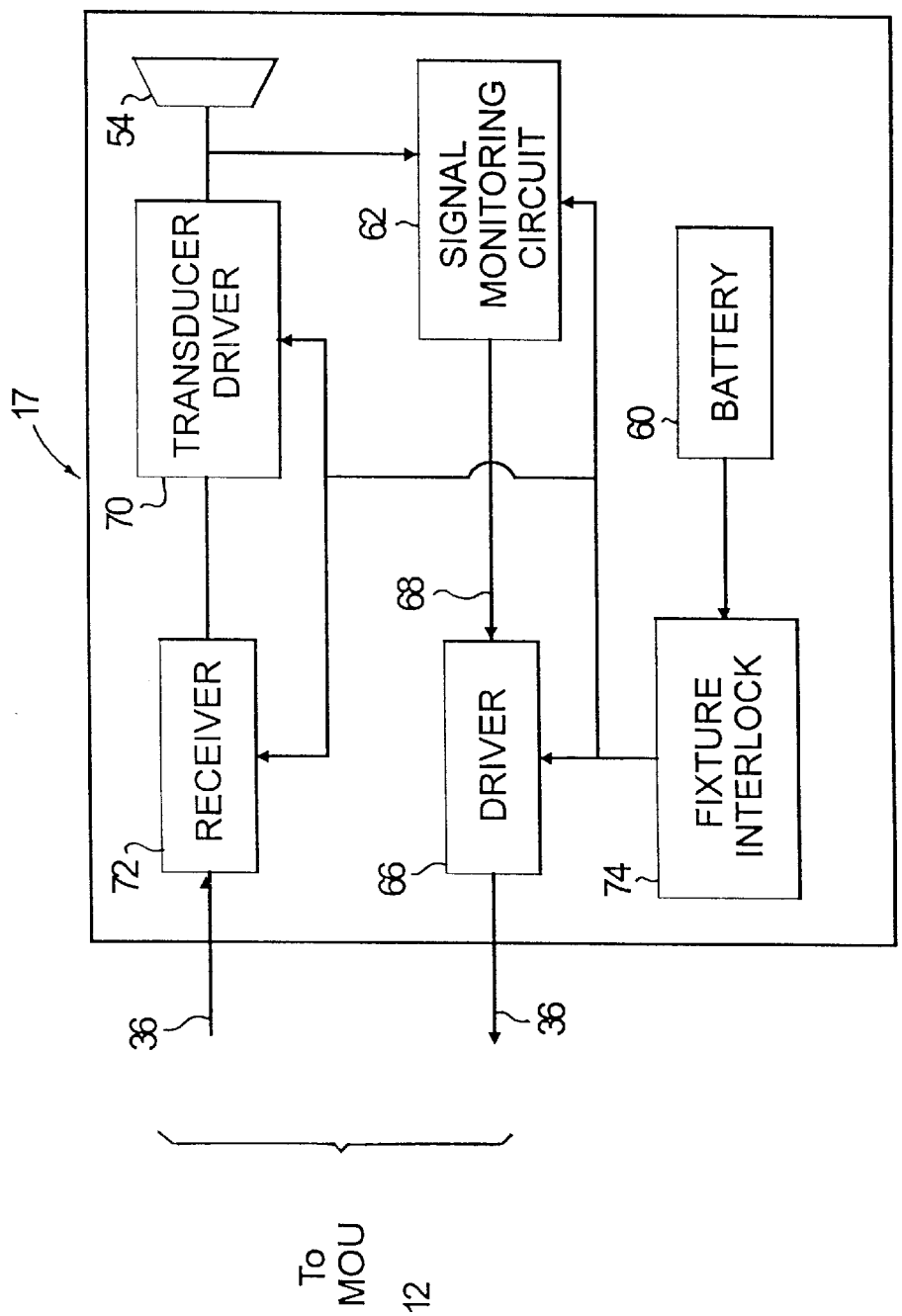
FIG. 4A is a block diagram of an alternative embodiment of the circuitry for the ultrasonic transducer assembly.

An alternative embodiment of the transducer assembly circuitry 17 is shown in FIG. 4A. In this embodiment, the ultrasonic transducer assembly 16 includes an internal battery 60 which supplies power to the components within the transducer assembly 16. For example, battery 60 supplies power to signal monitoring circuit 62 and signal driver 66. The signal monitoring circuit 62 provides, preferably, a digital output signal 68 which represents the waveform characteristics of the output of transducer driver 70. These characteristics can be displayed on a digital display and may include, for example, the frequency, pulse repetition frequency, the pulse width and the average output power of the transducer 54. The output signal 68 of signal monitoring circuit 62 is transferred to the signal generator within MOU 12 via driver 66 and cable 36. The signal generator may include a processor and a switch for regulating the signal characteristics. Control signals from the MOU 12 are received by receiver 72 via cable 36. Safety or fixture interlock 74, which may include switches on the outer surface of the placement module 14 or transducer assembly 16, ensures that the placement module 14 is properly positioned before providing power to the internal components of the transducer assembly 16.

Figure 5:
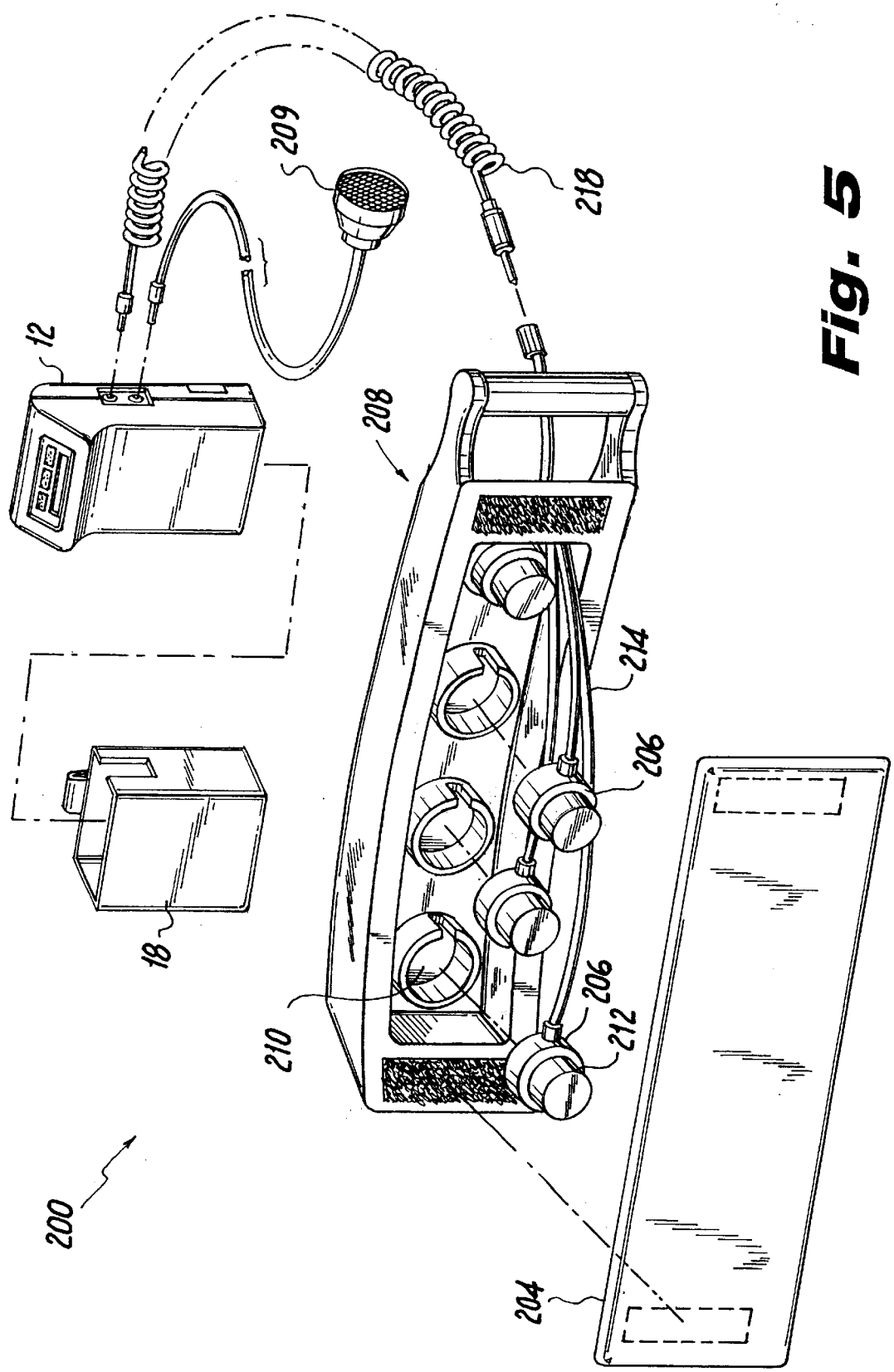
FIG. 5 is a perspective view of a second embodiment of the portable ultrasonic treatment apparatus, illustrating a main operating unit or controller and a placement module having a series of transducers.
Figure 6:
FIG. 6 is a perspective view of a patient wearing the portable treatment apparatus of FIG. 5.
Figure 7:
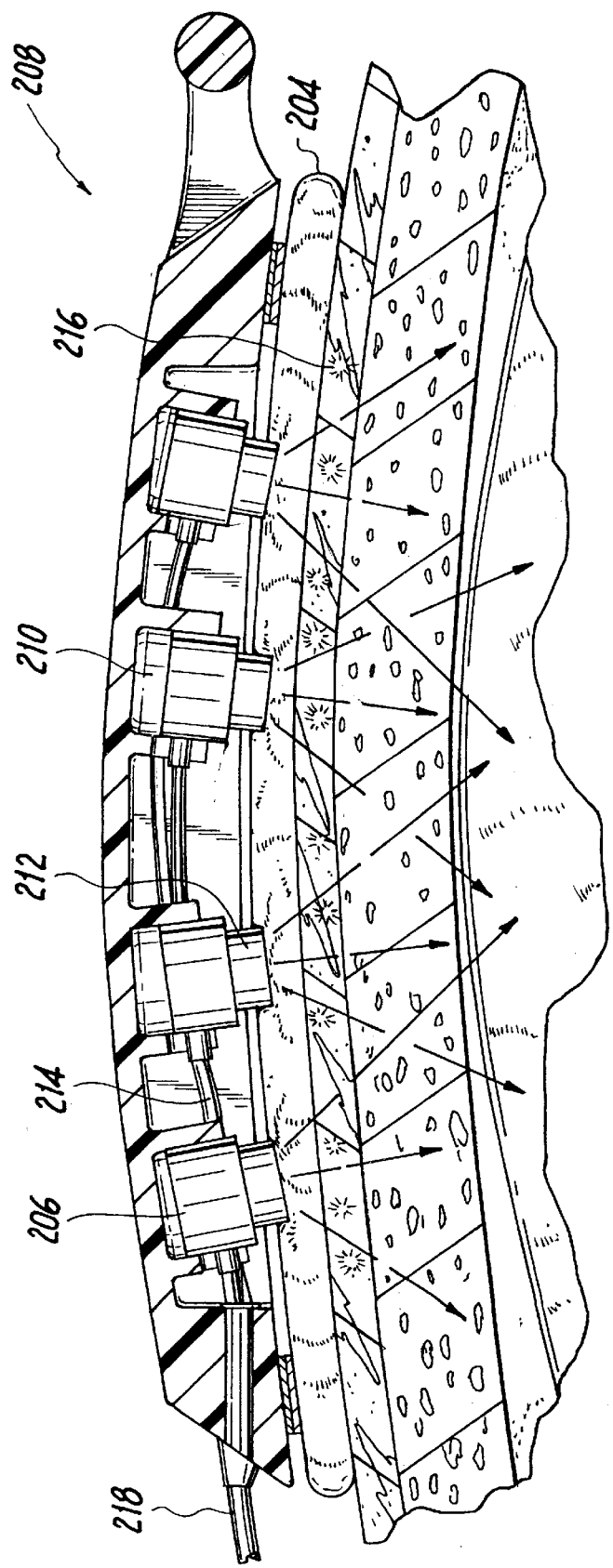
FIG. 7 is a cross-sectional view of the patient wearing the portable treatment apparatus of FIG. 5 taken along line 7—7 in FIG. 6.

A second embodiment of the portable ultrasonic treatment apparatus of the present invention is illustrated by FIGS. 5–7 and designated generally by numeral 200. The treatment apparatus 200 includes MOU 12, pouch 18, and a series of transducer assemblies 206 on a placement module 208. At least one sensor 209 is also included and coupled to MOU 12 for sensing the stimulation of the pain receptors by the sympathetic nervous system.

The transducer assemblies 206 can be placed within pockets 210 of the placement module 208 such that they lie over the pain receptors at the injury site. Each transducer assembly 206 includes a power transducer 212 connected to the MOU via wires 214 and cable 218. A gel-like substance 204 may be positioned between the transducer assemblies 206 and the injured part of the patient's body to prevent attenuation of the ultrasonic waves as they travel to the pain receptors 216, as shown by FIG. 7. The circuitry 17 for each transducer assembly may be similar to that disclosed for the first and second embodiments and schematically illustrated by FIGS. 4 and 4A.

In operation, the placement module 208 is positioned and firmly secured to the patient's body as shown by FIGS. 6 and 7, such that the transducer assemblies 206 and at least one sensor 209 lie over the pain receptors in the injured part of the body. Once the placement module 208 is properly positioned the transducers within the transducer assemblies 206 are excited for a pre-determined period of time after the at least one sensor 209 has sensed the stimulation of the pain receptors by the sympathetic nervous system. The sensor 209 may provide a signal to the MOU 12 once the sensor 209 no longer senses the stimulation of the pain receptors to disenable the transducer assemblies 206.

It is envisioned that the placement module 208 be constructed from suitable conductive plastics, such as conductive ABS plastics with either carbon, stainless steel, nickel or aluminum fibers to forego the use of wires 210 for connecting the transducer assemblies 206 to each other. In such an embodiment, the conductive placement module 208 would be used to electrically connect the transducer assemblies 206 to each other.

Figure 8:
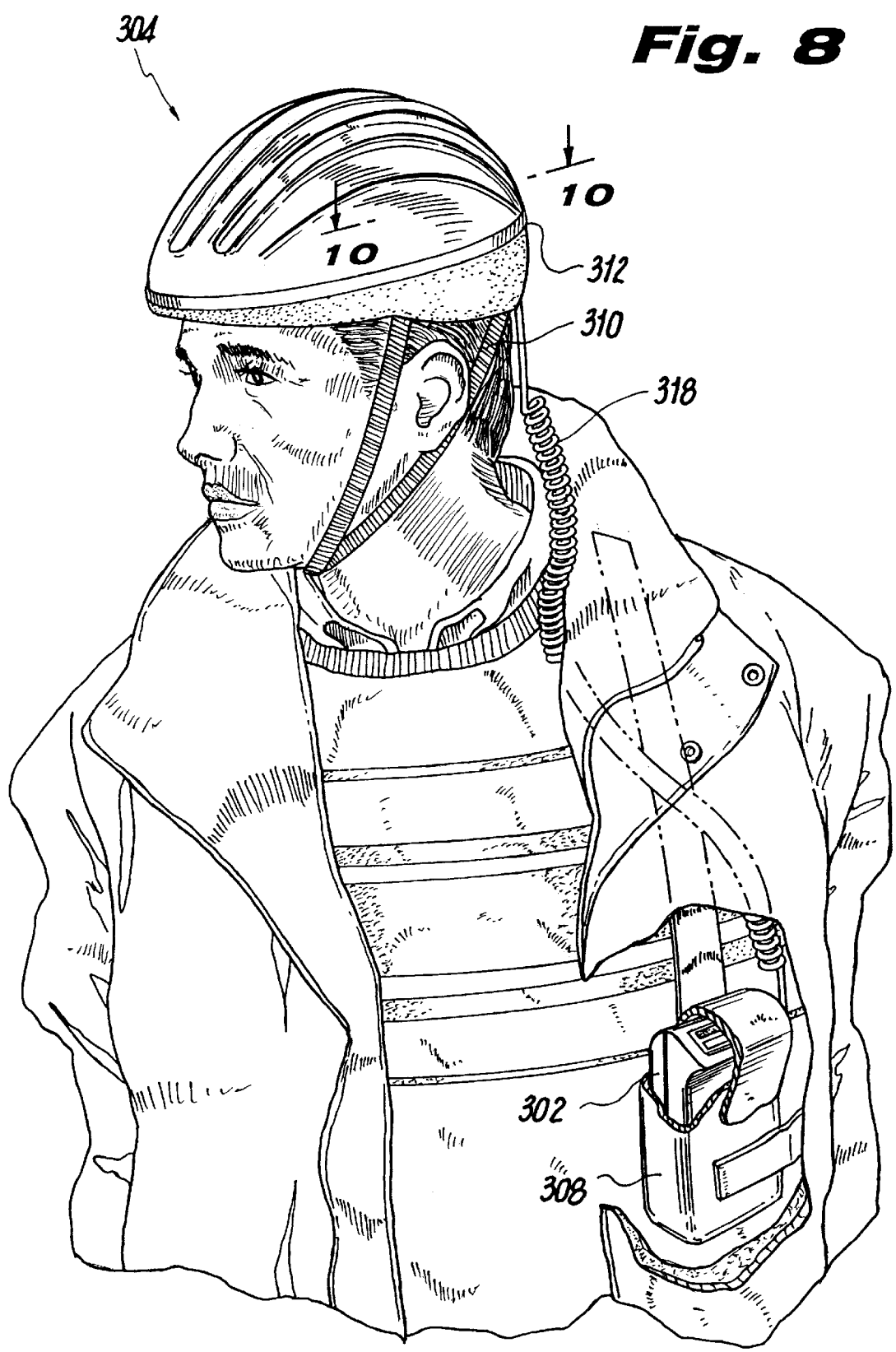
FIG. 8 is a perspective view of a patient wearing a portable treatment apparatus of a third embodiment configured for mounting a plurality of transducers in a plurality of configurations in proximity to pain receptors in the injured part of the body.
Figure 9:
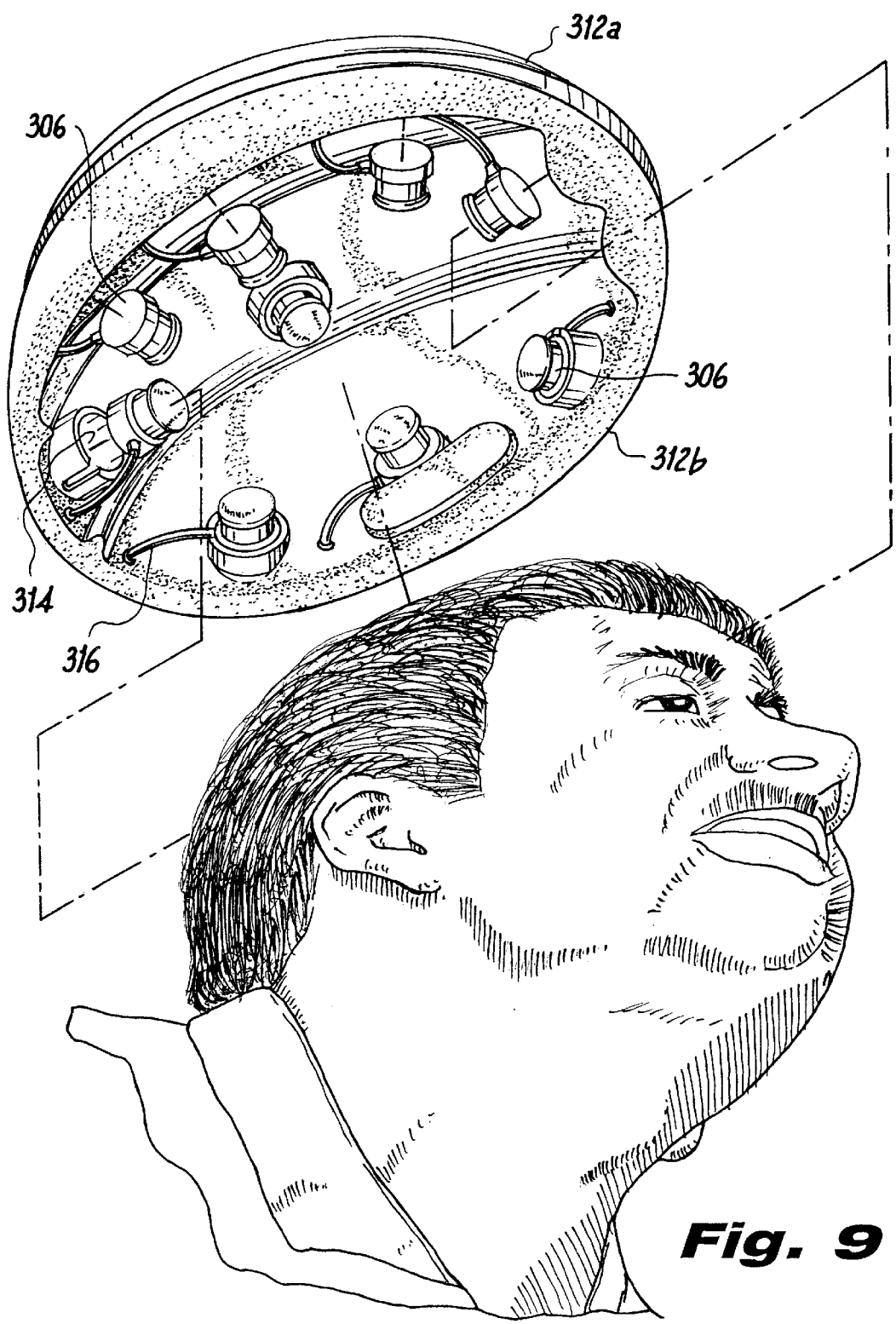
FIG. 9 is a perspective view of a placement module of the embodiment of FIG. 8 being placed on a patient.
Figure 10:
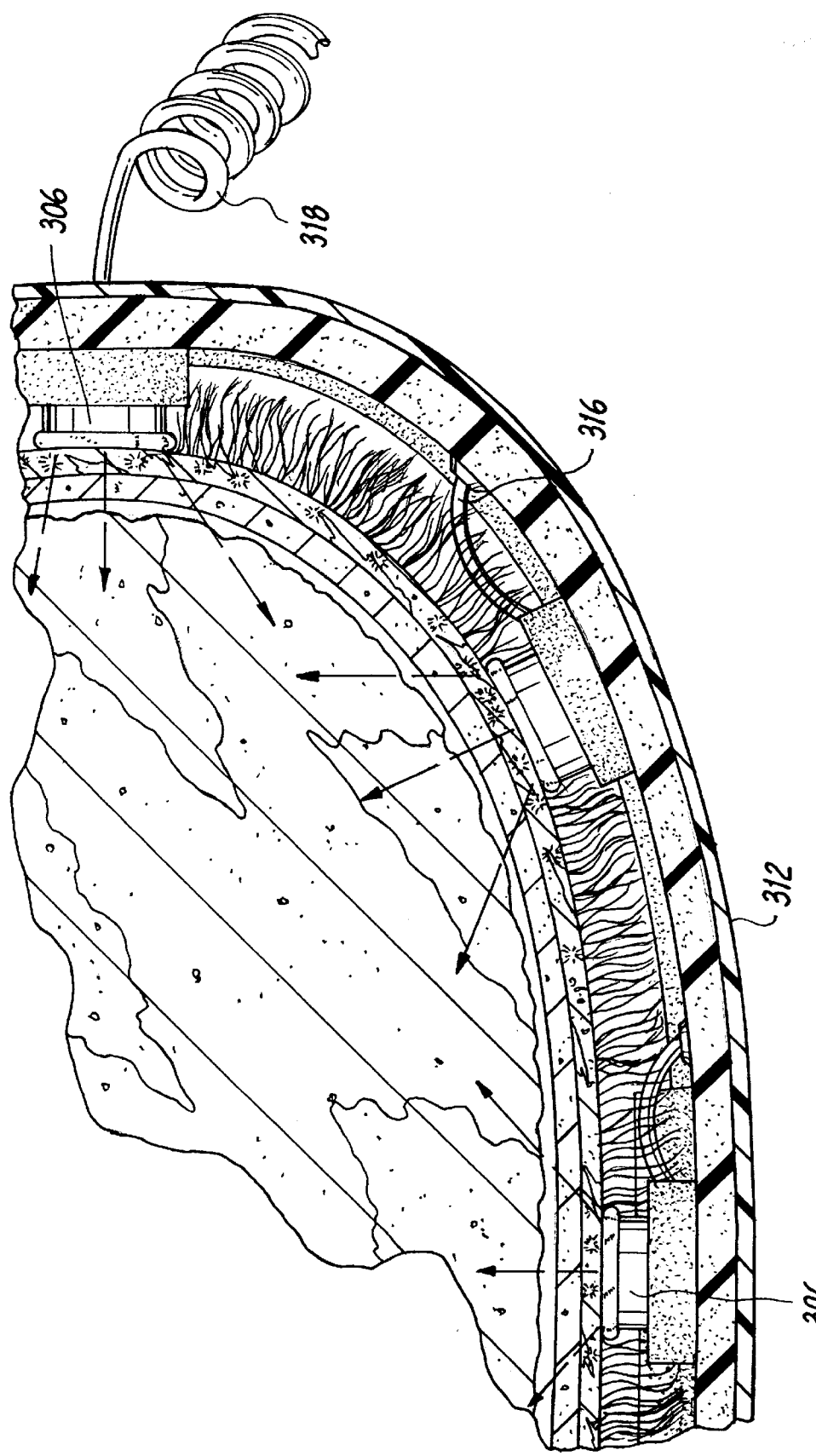
FIG. 10 is a cross-sectional view along line 10—10 of FIG. 8.

With reference to FIGS. 8–10, a third embodiment of the portable ultrasonic treatment apparatus of the present invention is illustrated. In this embodiment, the treatment apparatus 300 includes a MOU 302, a placement module 304, ultrasonic transducer assemblies 306, and a pouch 308 for providing patient mobility during treatment. The placement module 304 is comprised of a placement band 310 and a placement support 312 having half-sections 312a and 312b. The under-side of each half-section 312a and 312b includes pockets 314 for placement of transducer assemblies 306 therein. The transducer assemblies 306 may be arranged in a plurality of configurations within pockets 314 such that they lie over the injured part of the body. Each transducer assembly 306 is connected to the MOU 302 via wires 316 and cable 318 to power transducer assembly circuitry 17 within each assembly 306. The circuitry 17 may be similar to that disclosed for the first and second embodiments and schematically illustrated by FIGS. 4 and 4A.

In operation, transducers within transducer assemblies 306 are excited for a pre-determined period of time to impinge ultrasonic waves to the pain receptors in the injured part of the body as shown by FIG. 10.

Figure 11:
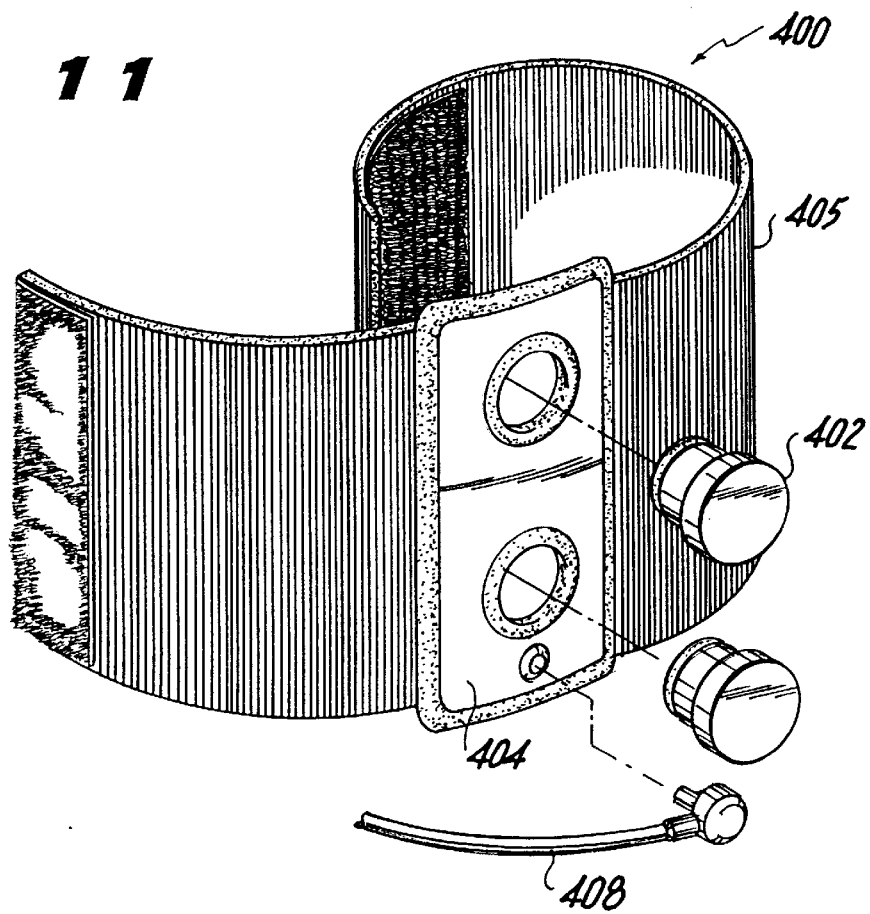
FIG. 11 is a perspective view of a portable treatment apparatus of a fourth embodiment configured for treating RSD.
Figure 13:
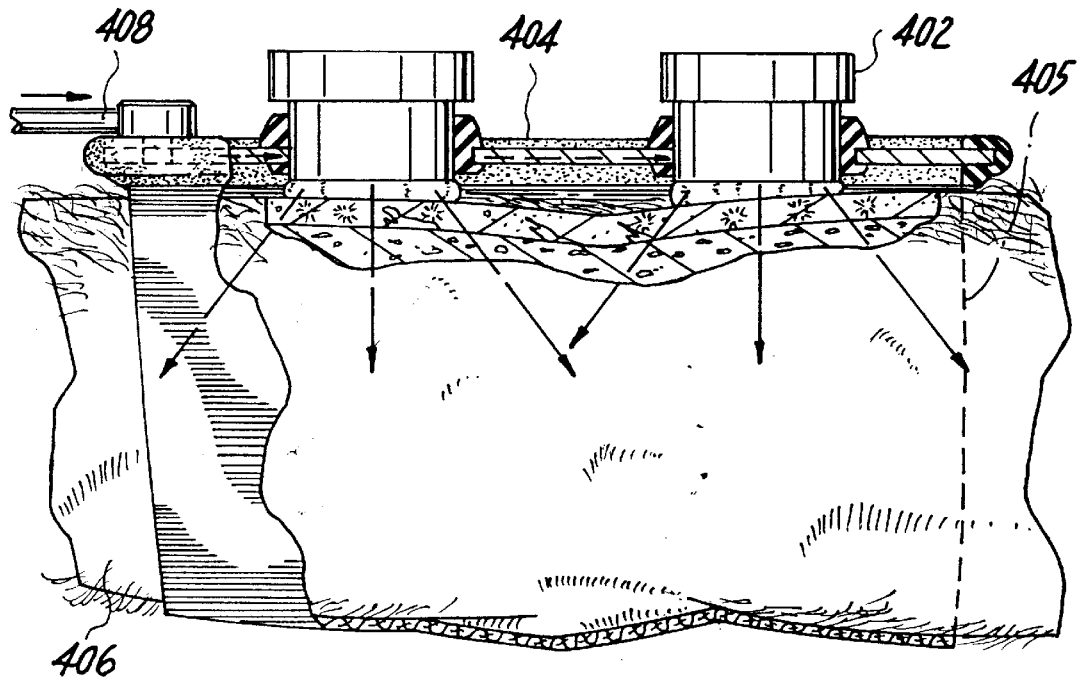
FIG. 13 is a cross-sectional view taken along line 13—13 in FIG. 12.
Figure 12:
FIG. 12 is a perspective view of a patient wearing the portable treatment apparatus of FIG. 11.

A fourth embodiment of the portable ultrasonic treatment apparatus of the present invention which is primarily suitable for the treatment of RSD is illustrated by FIGS. 11–13. In this embodiment, the apparatus 400 includes at least one ultrasonic transducer assembly 402 positioned on a conductive strip 404. The strip 404 is secured to a placement band 405 which is fitted against the injured part of the patient's body 406. The conductive strip 404 is connected via a cable 408 to a MOU 410 which contains circuitry for exciting ultrasonic transducer assembly 402 affixed to the conductive strip 404. The conductive strip 404 is preferably constructed from suitable conductive plastics such as conductive ABS plastics with either carbon, stainless steel, nickel or aluminum fibers to forego the use of wires for electrically connecting more than one ultrasonic transducer to the conductive strip 404.

In operation, the transducer assembly 402 is excited to impinge ultrasonic waves to the pain receptors in the injured part of the body as shown by FIG. 13. It is contemplated that during treatment a gel-like substance is positioned between the transducer assembly 402 and the patient's body to prevent attenuation of the ultrasonic waves.

A fifth embodiment of the portable ultrasonic treatment apparatus of the present invention which is primarily suitable for the treatment of RSD is illustrated by FIGS. 14 and 15. In this embodiment, the apparatus 500 includes at least one ultrasonic transducer assembly 502 positioned on an inner surface of a first support 504 and a second support 506 having straps 507 for strapping the supports 504, 506 to an appendage, such as an arm. A gel-lined tubular muff 508 is also included for being worn by the patient prior to strapping the two supports 504, 506 as shown by FIG. 15. The at least one ultrasonic transducer assembly 502 is connected via a cable 510 to a MOU 512 which contains circuitry for exciting ultrasonic transducer assembly 502.

In operation, the transducer assembly 502 is excited to impinge ultrasonic waves to the pain receptors in the injured part of the body. The gel-lined surface of the tubular muff 508 prevents the attenuation of the ultrasonic waves.

Figure 17:
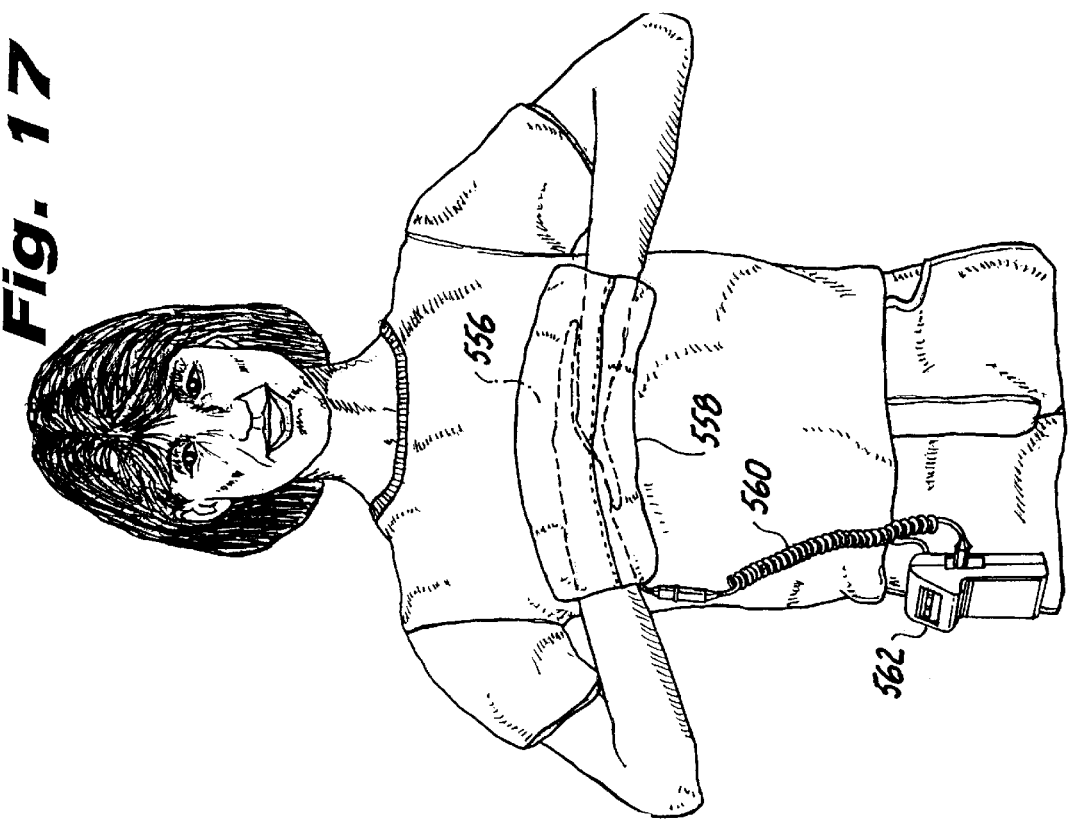
FIG. 17 is a perspective view of a patient wearing the portable treatment apparatus of FIG. 16.
Figure 16:
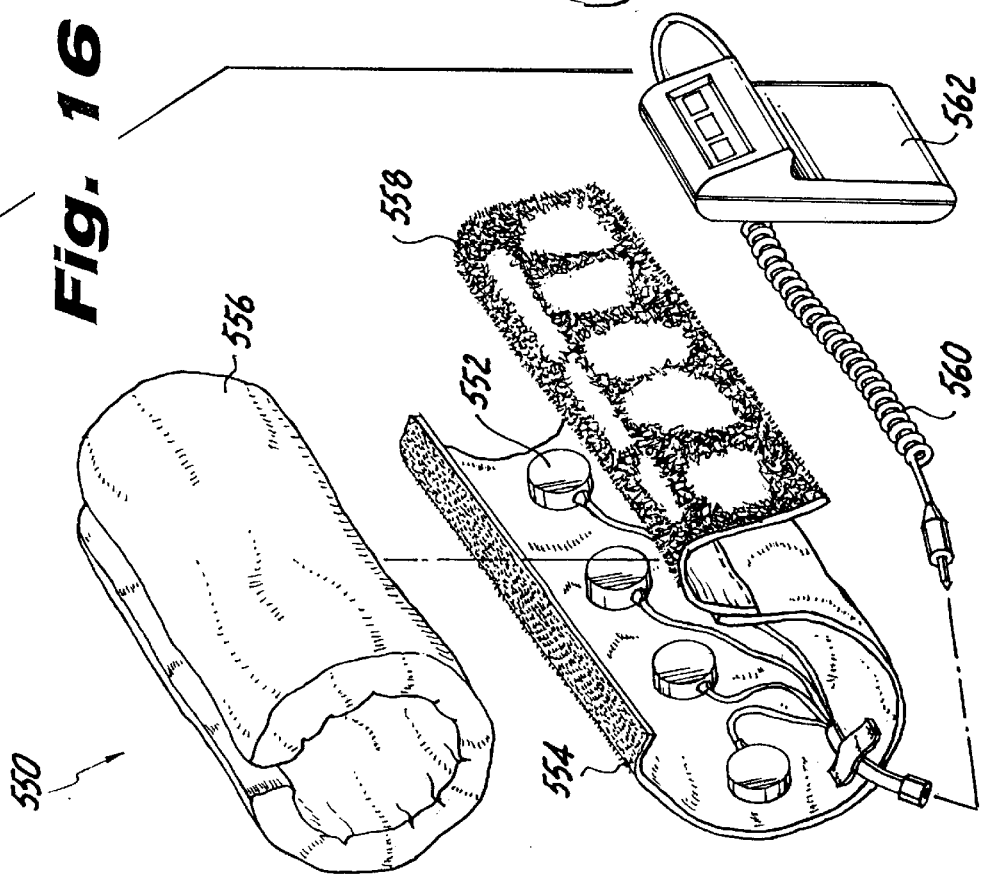
FIG. 16 is a perspective view of a portable treatment apparatus of a sixth embodiment configured for treating RSD.

A sixth embodiment of the portable ultrasonic treatment apparatus of the present invention which is primarily suitable for the treatment of RSD is illustrated by FIGS. 16 and 17. In this embodiment, the apparatus 550 includes at least one ultrasonic transducer assembly 552 positioned on an inner surface of an outer support layer 554. The outer support layer 554 wraps around a gel-lined tubular muff 556 and is affixed thereto by an elongated strap 558. The gel-lined tubular muff 556 is worn by the patient prior to strapping the outer support layer 554 to securely tighten the support layer 554 over the muff 556, as shown by FIG. 17. The at least one ultrasonic transducer assembly 552 is connected via a cable 560 to a MOU 562 which contains circuitry for exciting ultrasonic transducer assembly 552.

In operation, the transducer assembly 552 is excited to impinge ultrasonic waves to the pain receptors in the injured part of the body. The gel-lined surface of the tubular muff 556 prevents the attenuation of the ultrasonic waves.

Figure 20:
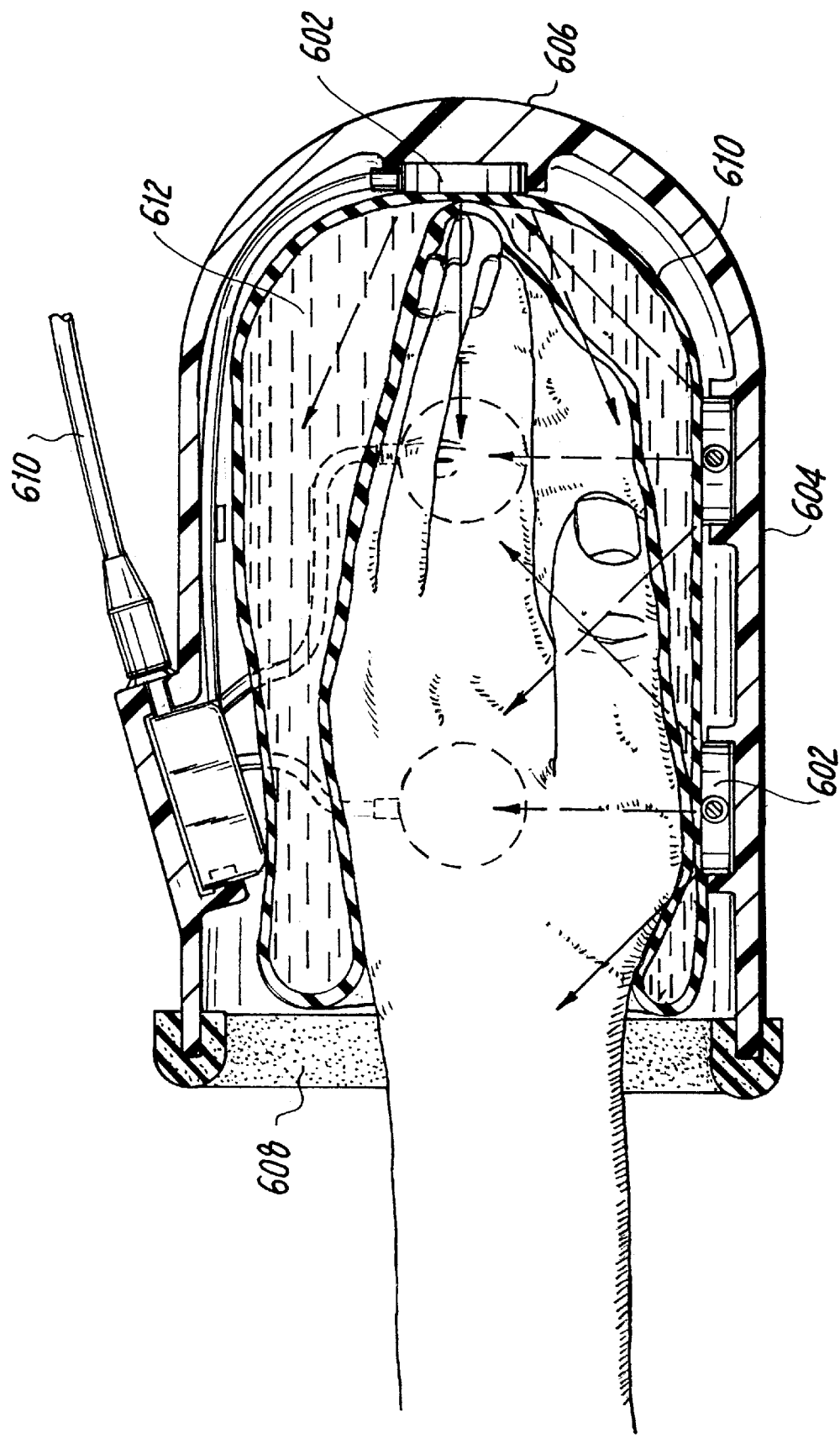
FIG. 20 is a cross-sectional view of a patient using the treatment apparatus of FIG. 18.

A seventh embodiment of the portable ultrasonic treatment apparatus of the present invention which is primarily suitable for the treatment of RSD is illustrated by FIGS. 18–20. In this embodiment, the apparatus 600 includes at least one ultrasonic transducer assembly 602 positioned on an inner surface of a cylindrical support 604 having a closed end 606 and an open end 608. A bag 610 lines the inner perimeter of the support 604 and is filled with gel 612. The at least one ultrasonic transducer assembly 602 is connected via a cable 614 to a MOU 616 which contains circuitry for exciting ultrasonic transducer assembly 602.

In operation, the patient places their hand within the cylindrical support 604, as shown by FIG. 19, and activates the MOU 616 to excite transducer assembly 602 to impinge ultrasonic waves to the pain receptors in the injured part of the body, as shown by FIG. 20. The gel 612 within the bag 610 prevents the attenuation of the ultrasonic waves.

Figure 21:
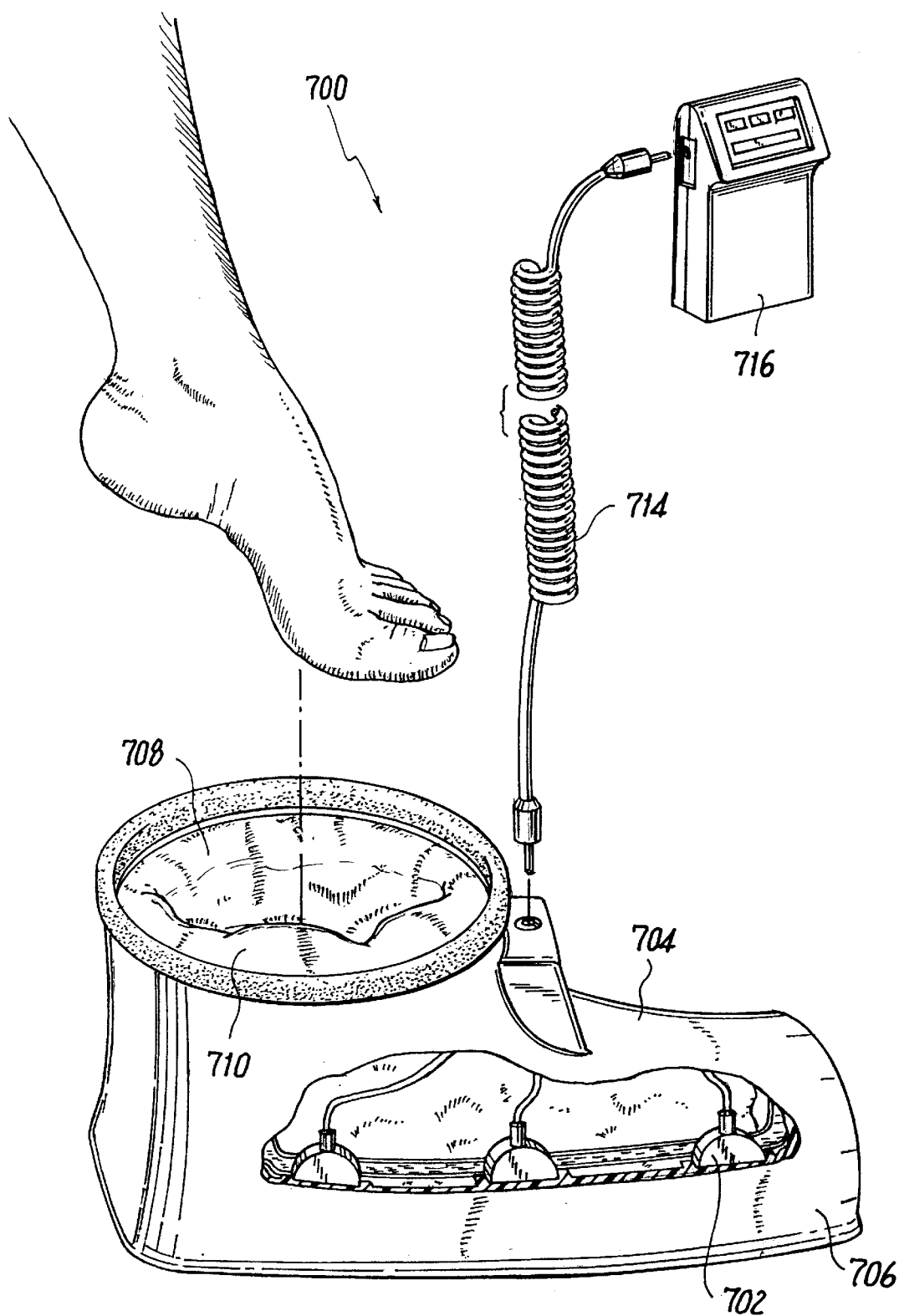
FIG. 21 is a perspective, partial cut-away view of a treatment apparatus of an eighth embodiment configured for treating RSD.
Figure 22:
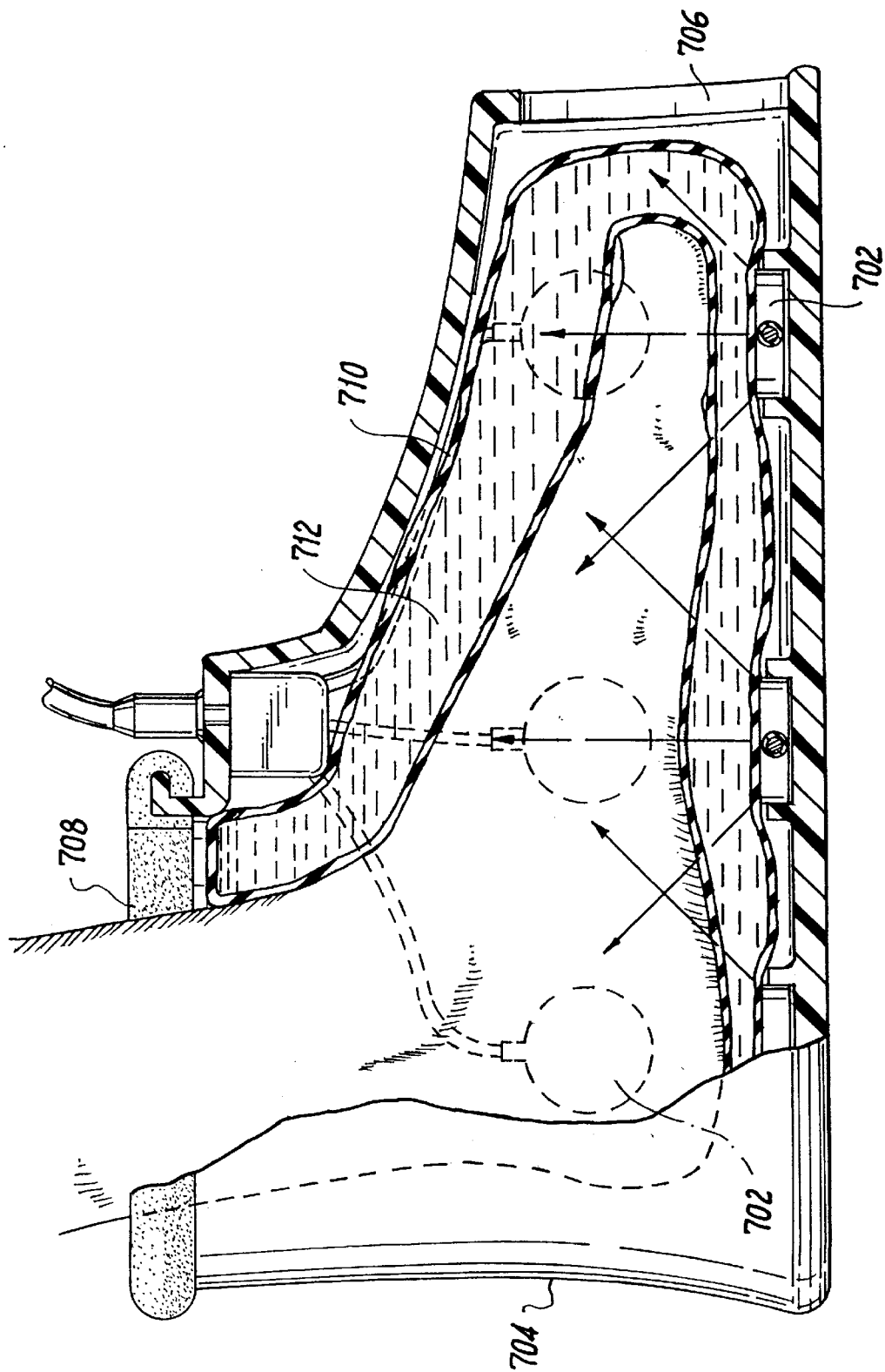
FIG. 22 is a cross-sectional view of a patient using the treatment apparatus of FIG. 21.

An eighth embodiment of the portable ultrasonic treatment apparatus of the present invention which is primarily suitable for the treatment of RSD is illustrated by FIGS. 21 and 22. In this embodiment, the apparatus 700 includes at least one ultrasonic transducer assembly 702 positioned on an inner surface of a foot-shaped support 704 having a closed end 706 and an open end 708. A bag 710 lines the inner perimeter of the support 704 and is filled with gel 712. The at least one ultrasonic transducer assembly 702 is connected via a cable 714 to a MOU 716 which contains circuitry for exciting ultrasonic transducer assembly 702.

In operation, the patient places their foot within the foot-shaped support 704 and activates the MOU 716 to excite transducer assembly 702 to impinge ultrasonic waves to the pain receptors in the injured part of the body, as shown by FIG. 22. The gel 712 within the bag 710 prevents the attenuation of the ultrasonic waves.

Figure 24:
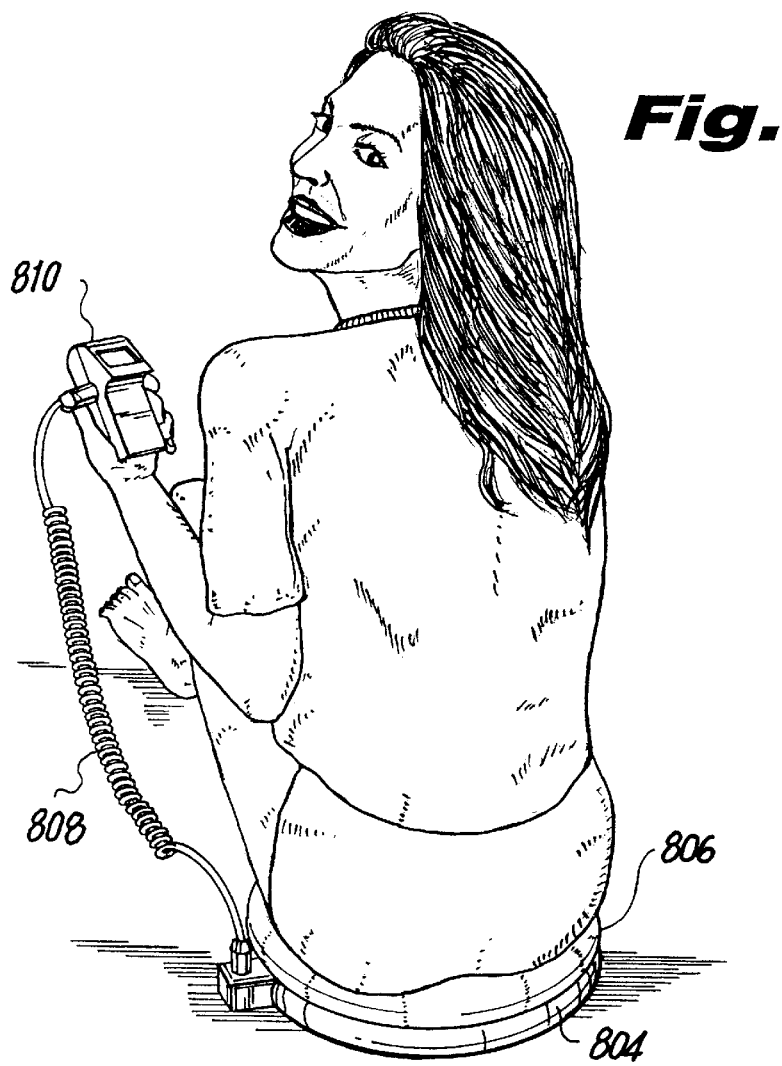
FIG. 24 is a perspective view of a patient using the treatment apparatus of FIG. 23.
Figure 23:
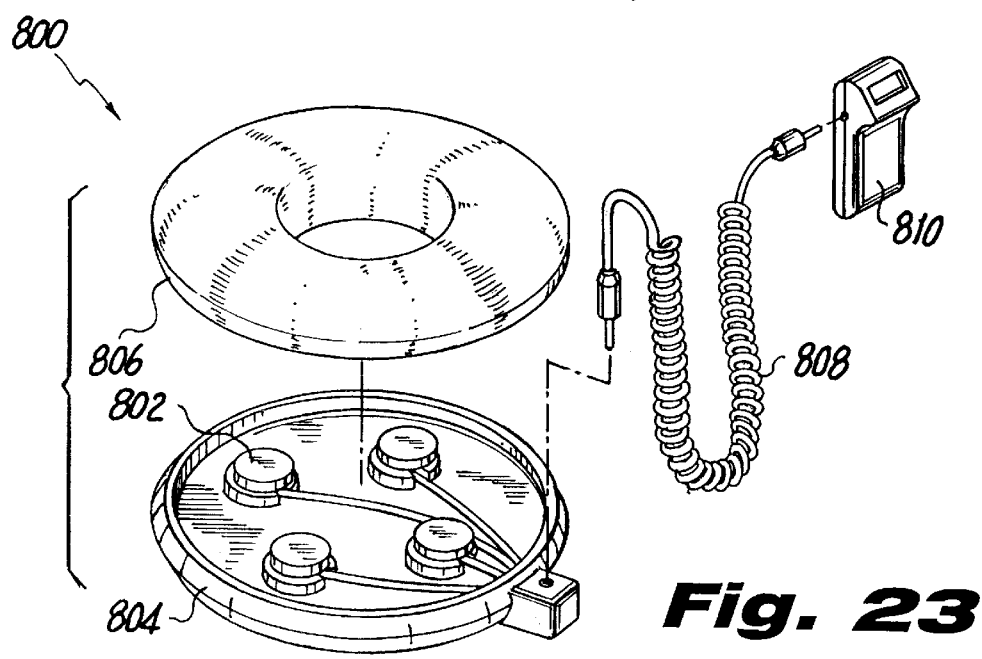
FIG. 23 is a perspective view of a treatment apparatus of a ninth embodiment configured for treating RSD.

A ninth embodiment of the portable ultrasonic treatment apparatus of the present invention which is primarily suitable for the treatment of RSD is illustrated by FIGS. 23 and 24. In this embodiment, the apparatus 800 includes at least one ultrasonic transducer assembly 802 positioned on an inner surface of a circular-disc support or basin 804. A ring-shaped bag 806 filled with a gel is dimensioned to rest on top of the support 804. The at least one ultrasonic transducer assembly 802 is connected via a cable 808 to a MOU 810 which contains circuitry for exciting ultrasonic transducer assembly 802.

In operation, the patient sits on the ring-shaped bag 806 and activates the MOU 810 to excite transducer assembly 802 to impinge ultrasonic waves to the pain receptors in the injured part of the body, as shown by FIG. 24. The bag 806 provides comfort to the patient and the gel within the bag 806 prevents the attenuation of the ultrasonic waves.

Figure 25:
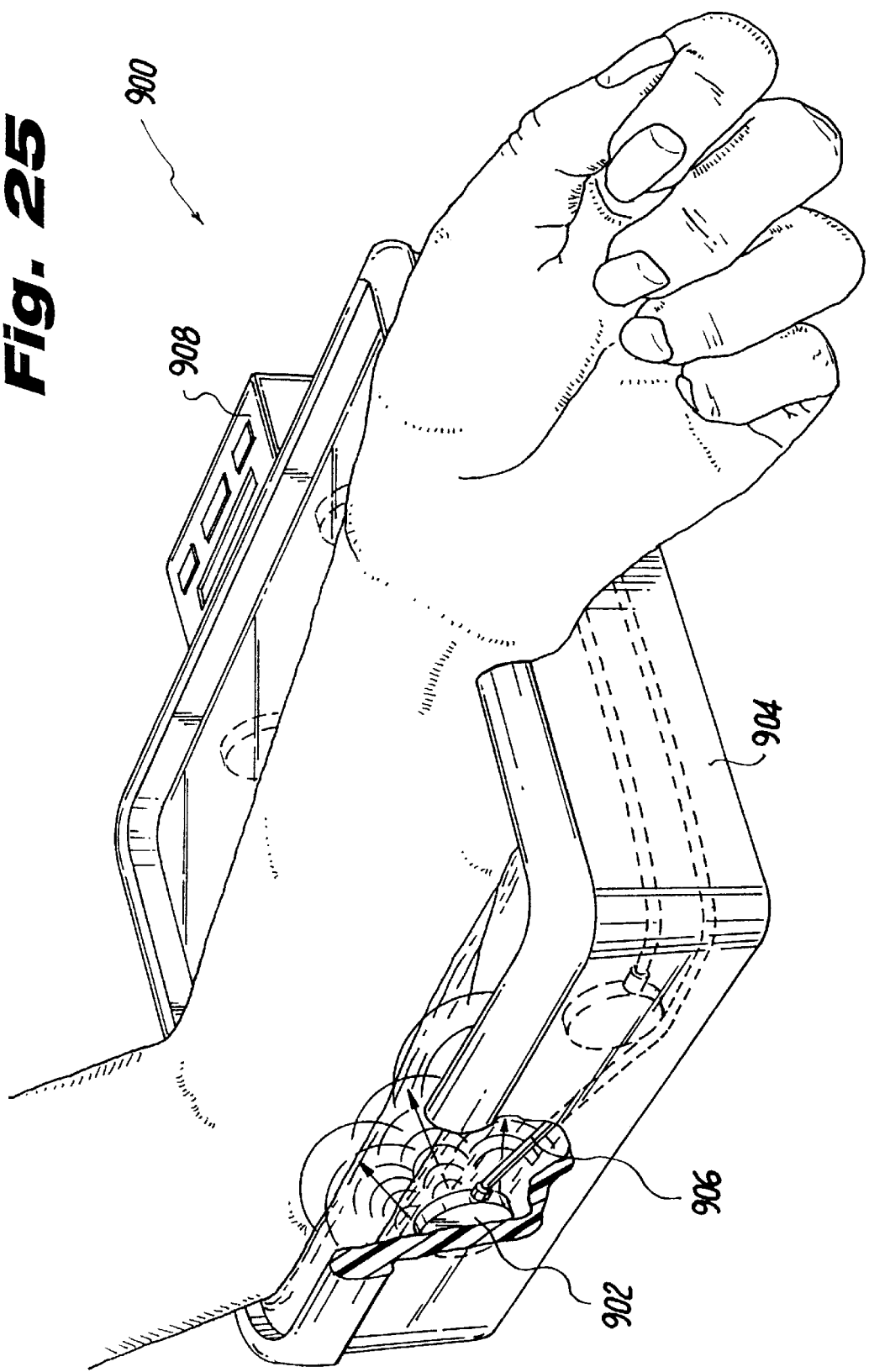
FIG. 25 is a perspective view of a treatment apparatus of a tenth embodiment configured for treating RSD.

A tenth embodiment of the ultrasonic treatment apparatus of the present invention which is primarily suitable for the treatment of RSD is illustrated by FIG. 25. In this embodiment, the apparatus 900 includes a plurality of ultrasonic transducer assemblies 902 positioned along the perimeter of a treatment basin 904. The treatment basin 904 is filled with a liquid, preferably water, to prevent the attenuation of the ultrasonic waves emitted by the plurality of ultrasonic transducer assemblies 902 during treatment. The ultrasonic transducer assemblies 902 are connected via wires 906 to an operating unit 908 which contains circuitry for exciting the ultrasonic transducer assemblies 902.

In operation, the patient places the injured part of the body within the treatment basin 904, as shown by FIG. 25. The transducer assemblies 902 are then excited to impinge ultrasonic waves to the pain receptors in the injured part of the body. A sensor may also be used for sensing stimulation of the pain receptors before the ultrasonic transducer assemblies 902 are excited.

It will be understood that various modifications can be made to the various embodiments of the present invention herein disclosed without departing from its spirit and scope. For example, various shapes of the pouch and signal generator are contemplated, as well as various types of construction materials. Also, various modifications may be made in the structural configuration of the placement module and the configuration of the components used to excite the ultrasonic transducer. For example, a sensor may be used with all the embodiments described herein for sensing the stimulation of the pain receptors. Therefore, the above description should not be construed as limiting the invention but merely as presenting preferred embodiments of the invention. Those skilled in the art will envision other modifications within the scope and spirit of the present invention as defined by the claims presented below.

What is claimed is:

1. A kit for ultrasonically treating reflex sympathetic dystrophy while maintaining patient mobility, which comprises:
   an ultrasonic transducer assembly having at least one ultrasonic transducer;
   a placement module configured to be worn by a patient, said placement module being configured to receive said transducer assembly such that when said placement module is worn said at least one ultrasonic transducer is positioned in proximity to pain receptors of the sympathetic nervous system;
   an ultrasonic signal generator positioned in said ultrasonic transducer assembly;
   a main operating unit; and
   a sensor coupled to said main operating unit for sensing stimulation of said pain receptors.

2. The kit according to claim 1, wherein said ultrasonic signal generator includes signal generator circuitry and an internal power source connected to said signal generator circuitry, and said signal generator circuitry including a processor and means for generating a pulsed RF signal.

3. The kit according to claim 2, wherein said signal generator circuitry is coupled to a display for displaying treatment sequence data.

4. The kit according to claim 1, further comprising safety interlock means to prevent inadvertent excitation of said at least one ultrasonic transducer.

5. The kit according to claim 1, wherein said main operating unit is positioned within a pouch worn by the patient to permit portable operation thereof.

6. The kit according to claim 1, wherein the placement module is constructed from a conductive material and said at least one ultrasonic transducer is provided on said placement module is electrically coupled to said main operating unit via said conductive material.

7. The kit according to claim 1, wherein the placement module is custom molded for a particular patient.

8. A kit for ultrasonically treating reflex sympathetic dystrophy while maintaining patient mobility, which comprises:
   a plurality of ultrasonic transducer assemblies each having an ultrasonic transducer;
   a treatment basin configured for placement of an injured part of a patient's body therein, said treatment basin being configured to receive said plurality of ultrasonic transducer assemblies such that when said injured part is placed within the treatment basin said ultrasonic transducers are positioned in proximity to pain receptors of the sympathetic nervous system;
   an ultrasonic signal generator positioned in each of said ultrasonic transducer assemblies;
   a main operating unit; and
   a sensor coupled to said main operating unit for sensing stimulation of said pain receptors.

9. The kit according to claim 8, wherein said ultrasonic signal generator includes signal generator circuitry and an internal power source connected to said signal generator circuitry, and said signal generator circuitry including a processor and means for generating a pulsed RF signal.

10. The kit according to claim 8, wherein said treatment basin is filled with water to minimize the attenuation of ultrasonic waves emitted by said plurality of ultrasonic transducer assemblies.

11. The kit according to claim 8, wherein said treatment basin is overlaid with a cushion to provide comfort to the patient.

12. The kit according to claim 11, wherein said cushion is filled with a gel-like substance to prevent the attenuation of ultrasonic waves emitted by said plurality of ultrasonic transducer assemblies.

13. A method for ultrasonically treating reflex sympathetic dystrophy comprising the following steps:
   providing a main operating unit having an internal power source coupled to an ultrasonic transducer assembly, said ultrasonic transducer assembly includes at least one ultrasonic transducer, an ultrasonic signal generator and signal generator circuitry therein;
   providing a placement module configured to receive said transducer assembly such that when an injured part of a patient's body is placed in proximity to said placement module, said at least one ultrasonic transducer is in proximity to pain receptors of the sympathetic nervous system;
   sensing the stimulation of said pain receptors; and
   exciting said at least one ultrasonic transducer to impinge ultrasonic waves at or near the pain receptors.

14. The method according to claim 13, wherein the placement module is a treatment basin.

15. A method for ultrasonically treating reflex sympathetic dystrophy while maintaining patient mobility, comprising the following steps:
   releasably securing at least one ultrasonic transducer coupled to a signal generator to a strip;

affixing said strip on a patient's such that said at least one transducer is in proximity to pain receptors of the sympathetic nervous system;

sensing the stimulation of said pain receptors; and exciting said at least one ultrasonic transducer by actuating said signal generator to impinge ultrasonic waves to the pain receptors.

16. The method according to claim 15, further including the step of:

connecting said at least one ultrasonic transducer to an operating unit, said operating unit having an internal power source for permitting patient mobility during treatment.

17. The method according to claim 15, further including the step of:

placing a gel-like substance between the at least one transducer and the patient to minimize attenuation of said ultrasonic waves.

* * * * *